(12) United States Patent
Jahns (10) Patent No.: US 7,118,566 B2
(45) Date of Patent: Oct. 10, 2006

(54) DEVICE AND METHOD FOR NEEDLE-LESS INTERSTITIAL INJECTION OF FLUID FOR ABLATION OF CARDIAC TISSUE

(75) Inventor: Scott E. Jahns, Husdon, WI (US)

(73) Assignee: Medtronic, Inc., Minneapolis, MN (US)

(*) Notice: Subject to any disclaimer, the term of this patent is extended or adjusted under 35 U.S.C. 154(b) by 104 days.

(21) Appl. No.: 10/356,909

(22) Filed: Feb. 3, 2003

(65) Prior Publication Data
US 2003/0216724 A1 Nov. 20, 2003

Related U.S. Application Data

(60) Provisional application No. 60/381,217, filed on May 16, 2002.

(51) Int. Cl.
*A61B 18/12* (2006.01)

(52) U.S. Cl. .................................... 606/41

(58) Field of Classification Search .......... 606/41–52; 607/96, 98
See application file for complete search history.

(56) References Cited

U.S. PATENT DOCUMENTS

| | | |
|---|---|---|
| 3,736,936 A | 6/1973 | Basiulis et al. |
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,061,135 A | 12/1977 | Widran et al. |

(Continued)

OTHER PUBLICATIONS

J. Thorac Cardiovascular Surg 1991; 101: 402-5—The Surgical Treatment of atrial fibrillation (Summary of the current concepts of the mechanisms of atrial flutter and atrial fibrillation) by James L. Cox, MD; Richard B. Schuessler, PHD; and John P. Boineau, MD.

(Continued)

*Primary Examiner*—Roy D. Gibson
*Assistant Examiner*—Aaron Roane
(74) *Attorney, Agent, or Firm*—Jeffrey J. Hohenshell (57) ABSTRACT

Methods and apparatus for delivering precise amounts of fluid under pressure into cardiac tissue for the purpose of facilitating ablation of the tissue along a desired lesion line. One method injects fluid under pressure through a discharge orifice in a needle-less injection device. The injected fluid can be a cytotoxic fluid and/or a highly conductive fluid injected in conjunction with radio frequency ablation to create an ablative virtual electrode. The injected fluid can provide deeper and narrower conduction paths and resulting lesions. Radio frequency ablation can be performed at the same time as the fluid injection, using the injection device as an electrode, or subsequent to the fluid injection, using a separate device. In some methods, the injected fluid is a protective fluid, injected to protect tissue adjacent to the desired lesion line. Fluid delivery can be endocardial, epicardial, and epicardial on a beating heart. The present methods find one use in performing maze procedures to treat atrial fibrillation.

16 Claims, 6 Drawing Sheets

U.S. PATENT DOCUMENTS

| | | |
|---|---|---|
| 4,063,560 A | 12/1977 | Thomas et al. |
| 4,072,152 A | 2/1978 | Linehan |
| 4,082,096 A | 4/1978 | Benson |
| 4,204,438 A | 5/1980 | Binaris et al. |
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |
| 4,377,168 A | 3/1983 | Rzasa et al. |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,719,825 A | 1/1988 | LaHaye et al. |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,936,281 A | 6/1990 | Stasz |
| 4,946,460 A | 8/1990 | Merry et al. |
| 4,985,030 A * | 1/1991 | Melzer et al. ............ 606/51 |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelina |
| 5,100,388 A | 3/1992 | Behl et al. |
| 5,108,390 A | 4/1992 | Potocky et al. |
| 5,147,355 A | 9/1992 | Friedman et al. |
| 5,178,133 A | 1/1993 | Pena |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,254,116 A | 10/1993 | Baust et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,295,956 A * | 3/1994 | Bales et al. ............... 604/30 |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,334,181 A | 8/1994 | Rubinsky et al. |
| 5,334,193 A | 8/1994 | Nardella |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,385,148 A | 1/1995 | Lesh et al. |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,423,807 A | 6/1995 | Milder |
| 5,423,811 A | 6/1995 | Imran et al. |
| 5,427,119 A | 6/1995 | Swartz et al. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,443,463 A | 8/1995 | Stern et al. |
| 5,443,470 A | 8/1995 | Stern et al. |
| 5,450,843 A | 9/1995 | Moll et al. |
| 5,452,582 A | 9/1995 | Longsworth |
| 5,452,733 A | 9/1995 | Sterman et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,558,671 A | 9/1996 | Yates |
| 5,560,362 A | 10/1996 | Silwa, Jr. et al. |
| 5,562,720 A | 10/1996 | Stern et al. |
| 5,569,241 A | 10/1996 | Edwards |
| 5,571,088 A | 11/1996 | Lennox et al. |
| 5,571,215 A | 11/1996 | Sterman et al. |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,607,462 A | 3/1997 | Imran |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,656,029 A | 8/1997 | Imran et al. |
| 5,658,278 A | 8/1997 | Imran et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |
| 5,681,278 A | 10/1997 | Igo et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |

| Patent No. | Date | Inventor |
|---|---|---|
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,713,942 A | 2/1998 | Stern |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Lanard |
| 5,722,402 A | 3/1998 | Swanson et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,735,290 A | 4/1998 | Nelson et al. |
| 5,755,760 A | 5/1998 | Maguire et al. |
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,797,960 A | 8/1998 | Stevens et al. |
| 5,800,428 A | 9/1998 | Nelson et al. |
| 5,800,482 A | 9/1998 | Pomeranz et al. |
| 5,810,802 A | 9/1998 | Panescu et al. |
| 5,827,216 A | 10/1998 | Igo et al. |
| 5,836,947 A | 11/1998 | Fleischman et al. |
| 5,840,030 A | 11/1998 | Ferek-Petric et al. |
| 5,844,349 A | 12/1998 | Oakley et al. |
| 5,846,187 A | 12/1998 | Wells et al. |
| 5,846,191 A | 12/1998 | Wells et al. |
| 5,849,028 A | 12/1998 | Chen |
| 5,871,523 A | 2/1999 | Fleischman et al. |
| 5,871,525 A | 2/1999 | Edwards et al. |
| 5,873,845 A | 2/1999 | Cline et al. |
| 5,876,399 A | 3/1999 | Chia et al. |
| 5,879,295 A | 3/1999 | Li et al. |
| 5,879,296 A | 3/1999 | Ockuly et al. |
| 5,881,732 A | 3/1999 | Sung et al. |
| 5,882,346 A | 3/1999 | Pomeranz et al. |
| 5,885,278 A | 3/1999 | Fleischman |
| 5,893,848 A | 4/1999 | Negus et al. |
| 5,895,417 A | 4/1999 | Pomeranz et al. |
| 5,897,553 A | 4/1999 | Mulier et al. |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,927,284 A | 7/1999 | Borst et al. |
| 5,928,191 A | 7/1999 | Houser et al. |
| 5,931,810 A | 8/1999 | Grabek |
| 5,931,848 A | 8/1999 | Saadat |
| 5,954,661 A | 9/1999 | Greenspon et al. |
| 5,971,980 A | 10/1999 | Sherman |
| 5,971,983 A | 10/1999 | Lesh |
| 5,993,447 A | 11/1999 | Blewett et al. |
| 6,007,499 A | 12/1999 | Martin et al. |
| 6,012,457 A | 1/2000 | Lesh |
| 6,016,811 A | 1/2000 | Knopp et al. |
| 6,042,556 A | 3/2000 | Beach et al. |
| 6,063,081 A | 5/2000 | Mulier et al. |
| 6,071,279 A | 6/2000 | Whayne et al. |
| 6,088,894 A | 7/2000 | Oakley et al. |
| 6,096,037 A * | 8/2000 | Mulier et al. .................. 606/49 |
| 6,113,592 A | 9/2000 | Taylor |
| 6,117,101 A | 9/2000 | Diederich et al. |
| 6,120,496 A | 9/2000 | Whayne et al. |
| 6,142,993 A | 11/2000 | Whayne et al. |
| 6,142,994 A | 11/2000 | Swanson et al. |
| 6,152,920 A | 11/2000 | Thompson et al. |
| 6,161,543 A | 12/2000 | Cox et al. |
| 6,165,174 A | 12/2000 | Jacobs et al. |
| 6,217,528 B1 | 4/2001 | Koblish et al. |
| 6,217,576 B1 | 4/2001 | Tu et al. |
| 6,224,592 B1 | 5/2001 | Eggers et al. |
| 6,231,518 B1 | 5/2001 | Grabek et al. |
| 6,231,591 B1 * | 5/2001 | Desai .......................... 606/210 |
| 6,235,024 B1 | 5/2001 | Tu |
| 6,237,605 B1 | 5/2001 | Vaska et al. |
| 6,238,347 B1 | 5/2001 | Nix et al. |
| 6,238,393 B1 | 5/2001 | Mulier et al. |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,128 B1 | 6/2001 | Knopp et al. |
| 6,270,471 B1 | 8/2001 | Hechel et al. |
| 6,293,943 B1 | 9/2001 | Panescu et al. |
| 6,296,619 B1 | 10/2001 | Brisken et al. |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,325,797 B1 | 12/2001 | Stewart et al. |
| 6,328,736 B1 | 12/2001 | Mulier et al. |
| 6,332,881 B1 | 12/2001 | Carner et al. |
| 6,358,248 B1 | 3/2002 | Mulier et al. |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,419,648 B1 | 7/2002 | Vitek et al. |
| 6,425,867 B1 | 7/2002 | Vaezy et al. |
| 6,430,426 B1 | 8/2002 | Avitall |
| 6,440,130 B1 | 8/2002 | Mulier et al. |
| 6,443,952 B1 | 9/2002 | Mulier et al. |
| 6,447,507 B1 | 9/2002 | Bednarek et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B1 | 11/2002 | Mulier |
| 6,477,396 B1 | 11/2002 | Mest et al. |
| 6,484,727 B1 | 11/2002 | Vaska et al. |
| 6,488,680 B1 | 12/2002 | Francischelli |
| 6,502,575 B1 | 1/2003 | Jacobs et al. |
| 6,514,250 B1 | 2/2003 | Jahns et al. |
| 6,527,767 B1 | 3/2003 | Wang et al. |
| 6,537,248 B1 | 3/2003 | Mulier |
| 6,537,272 B1 | 3/2003 | Hoey |
| 6,558,382 B1 | 5/2003 | Jahns |
| 6,584,360 B1 | 6/2003 | Francischelli |
| 6,585,732 B1 | 7/2003 | Mulier |
| 6,605,084 B1 | 8/2003 | Acker et al. |
| 6,610,055 B1 | 8/2003 | Swanson et al. |
| 6,610,060 B1 | 8/2003 | Mulier |
| 6,613,048 B1 | 9/2003 | Mulier et al. |
| 6,645,199 B1 | 11/2003 | Jenkins et al. |

| | | |
|---|---|---|
| 6,648,883 B1 | 11/2003 | Francischelli |
| 6,656,175 B1 | 12/2003 | Francischelli |
| 6,663,627 B1 | 12/2003 | Francischelli |
| 6,692,450 B1 | 2/2004 | Coleman |
| 6,699,240 B1 | 3/2004 | Francischelli |
| 6,702,811 B1 | 3/2004 | Stewart et al. |
| 6,706,038 B1 | 3/2004 | Francischelli |
| 6,706,039 B1 | 3/2004 | Mulier |
| 6,716,211 B1 | 4/2004 | Mulier |
| 6,736,810 B1 | 5/2004 | Hoey |
| 6,755,827 B1 | 6/2004 | Mulier |
| 6,764,487 B1 | 7/2004 | Mulier |
| 6,773,433 B1 | 8/2004 | Stewart et al. |
| 6,776,780 B1 | 8/2004 | Mulier |
| 6,807,968 B1 | 10/2004 | Francischelli |
| 6,827,715 B1 | 12/2004 | Francischelli |
| 6,849,073 B1 | 2/2005 | Hoey |
| 6,858,028 B1 | 2/2005 | Mulier |
| 6,887,238 B1 | 5/2005 | Jahns |
| 6,899,711 B1 | 5/2005 | Stewart et al. |
| 6,905,475 B1 | 6/2005 | Hauschild et al. |
| 6,911,019 B1 | 6/2005 | Mulier |
| 6,916,318 B1 | 7/2005 | Francischelli |
| 6,936,046 B1 | 8/2005 | Hissong |
| 6,949,097 B1 | 9/2005 | Stewart et al. |
| 6,949,098 B1 | 9/2005 | Mulier |
| 6,960,205 B1 | 11/2005 | Jahns |
| 6,962,589 B1 | 11/2005 | Mulier |
| 2003/0045872 A1 | 3/2003 | Jacobs |
| 2003/0144656 A1 | 7/2003 | Ocel |
| 2003/0191462 A1 | 10/2003 | Jacobs |
| 2003/0216724 A1 | 11/2003 | Jahns |
| 2004/0002647 A1 | 1/2004 | Desai |
| 2004/0015106 A1 | 1/2004 | Coleman |
| 2004/0015219 A1 | 1/2004 | Francischelli et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Christian |

OTHER PUBLICATIONS

J. Thorac Cardiovasc Surg 1991; 101: 584-92—The surgical treatment of atrial fibrillation (Surgical Technique) by James L. Cox, MD.

Ann Thorac Surg 1996; 62: 1796-800 / Simple Left Atrial Procedure for Chronic Atrial Fibrillation Associated With Mitral Valve Disease by Taijiro Sueda, MD; Hideyuki Nagata, MD; Hiroo Shikata, MD; Kazumasa Orihashi, MD; Satoru Morita, MD; Masafumi Sueshiro, MD; Kenji Okada, MD and Yuichiro Matsuura, MD.

PACE vol. 15 (Supplement September) 1992 pp. 1368-1373 / Transcoronary Chemical Ablation of Arrhythmias by Paul Nellens; Sinan Gursoy; Erik Andries and Pedro Brugada.

European Heart Journal, vol. 12, 1991, pp. 1234-1237 / Chemical ablation by subendocardial injection of ethanol via catheter—preliminary results in the pig heart by P. Weismuller; U. Mayer; P. Richter; F. Heieck; M. Kochs and V. Hombach.

Chitwood, "Will C. Sealy, MD: The Father of Arrhythmia Surgery—The Story of the Fisherman with a Fast Pulse," Annals of Thoracic Surgery 58:1228-1239, 1994.

Gallagher et al., "Cryosurgical Ablation of Accessory Atrioventrical Connections: A Method for Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Technique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery, vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): I-594.

Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Nardella, "Radio Frequency Energy and Impedance Feedback," SPIE vol. 1068, Catheter Based Sensing and Imaging Technology (1989).

Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:I450,#2519.

Jais et al., "Catheter Ablation for Paroxysmal Atrial Fibrillation: High Success Rates with Ablation in the Left Atrium," Circulation (Nov. 1996) 94:I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996:94(Supp 1):I-493, #2889.

Cox et al., "An 8 1/2 Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

* cited by examiner

DEVICE AND METHOD FOR NEEDLE-LESS INTERSTITIAL INJECTION OF FLUID FOR ABLATION OF CARDIAC TISSUE

RELATED APPLICATIONS

The present application claims the benefit of U.S. provisional patent application Ser. No. 60/381,217, filed May 16, 2002, titled DEVICE AND METHOD FOR ABLATION OF CARDIAC TISSUE, herein incorporated by reference in its entirety. The present application is related to commonly assigned U.S. patent application Ser. No. 10/356,868, filed on Feb. 3, 2003, titled DEVICE AND METHOD FOR ABLATION OF CARDIAC TISSUE.

FIELD OF THE INVENTION

The present invention relates generally to the field of devices for cardiac surgery, and more specifically to devices for ablation of cardiac tissue.

BACKGROUND OF THE INVENTION

The present invention is directed toward treatment of tachyarrhythmias, which are heart rhythms in which one or more chambers of the heart exhibit an excessively fast rhythm. In particular, the present invention is directed toward treatment of tachycardias, which are due to the presence of ectopic foci within the cardiac tissue or due to the presence of aberrant condition pathways within the cardiac tissue.

There are many medical treatments that involve instances of cutting, ablating, coagulating, destroying, or otherwise changing the physiological properties of tissue. These techniques can be used beneficially to change the electrophysiological properties of tissue. For example, ablation of cardiac tissue can be used to cure various cardiac conditions. Normal sinus rhythm of the heart begins with the sinoatrial node (or "SA node") generating a depolarization wave front. The impulse causes adjacent myocardial tissue cells in the atria to depolarize, which in turn causes adjacent myocardial tissue cells to depolarize. The depolarization propagates across the atria, causing the atria to contract and empty blood from the atria into the ventricles. The impulse is next delivered via the atrioventricular node (or "AV node") and the bundle of HIS (or "HIS bundle") to myocardial tissue cells of the ventricles. The depolarization of these cells propagates across the ventricles, causing the ventricles to contract. This conduction system results in the described, organized sequence of myocardial contraction leading to a normal heartbeat.

Sometimes aberrant conductive pathways develop in heart tissue, which disrupt the normal path of depolarization events. For example, anatomical obstacles in the atria or ventricles can disrupt the normal propagation of electrical impulses. These anatomical obstacles (called "conduction blocks") can cause the electrical impulse to degenerate into several circular wavelets that circulate about the obstacles. These wavelets, called "reentry circuits," disrupt the normal activation of the atria or ventricles.

The aberrant conductive pathways create abnormal, irregular, and sometimes life-threatening heart rhythms, called arrhythmias. An arrhythmia can take place in the atria, for example, as in atrial tachycardia, atrial fibrillation or atrial flutter. The arrhythmia can also take place in the ventricle, for example, as in ventricular tachycardia.

The lesions used to treat atrial fibrillation, are typically long and thin and are carefully placed to interrupt the conduction routes of the most common reentry circuits. More specifically, the long thin lesions are used to create a maze pattern that creates a convoluted path for electrical propagation within the left and right atria. The lesions direct the electrical impulse from the SA node along a specified route through all regions of both atria, causing uniform contraction required for normal atrial transport function. The lesions finally direct the impulse to the AV node to activate the ventricles, restoring normal atrioventricular synchrony. Several surgical approaches have been developed with the intention of treating atrial fibrillation. One particular example is known as the "maze procedure," as is disclosed by Cox, J L et al. in "The surgical treatment of atrial fibrillation. I. Summary" Thoracic and Cardiovascular Surgery 101(3), pp. 402–405 (1991); and also by Cox, J L in "The surgical treatment of atrial fibrillation. IV. Surgical Technique", Thoracic and Cardiovascular Surgery 101(4), pp. 584–592 (1991), both of which are incorporated by reference herein in their entireties. In general, the "maze" procedure is designed to relieve atrial arrhythmia by restoring effective atrial systole and sinus node control through a prescribed pattern of incisions about the tissue wall. In the early clinical experiences reported, the "maze" procedure included surgical incisions in both the right and the left atrial chambers. However, more recent reports predict that the surgical "maze" procedure may be substantially efficacious when performed only in the left atrium, such as is disclosed in Sueda et al., "Simple Left Atrial Procedure for Chronic Atrial Fibrillation Associated With Mitral Valve Disease" (1996), which is incorporated herein by reference in its entirety.

When modifying the electrophysiological properties of cardiac tissue by ablation, or by other means of destroying tissue to create lesions, physicians must carefully place the lesions. Otherwise, tissue will be unnecessarily destroyed. In addition, the heart is in close proximity to nerves and other nervous tissue and the destruction of this tissue will result in severe harm to the patient. Anatomical methods are used to locate the areas to be ablated or otherwise modified. In other words, the physician locates key structures such as the mitral valve annulus and the pulmonary veins. Lesions are typically formed that block propagations near these structures. Additional lesions are then formed which connect these lesions and complete the so-called "maze pattern." However, the exact lesion pattern, and number of lesions created, can vary from patient to patient.

The surgical "maze procedure" as performed in the left atrium generally includes forming vertical incisions from the two superior pulmonary veins and terminating in the region of the mitral valve annulus, traversing the inferior pulmonary veins en route. An additional horizontal line also connects the superior ends of the two vertical incisions. Thus, the atrial wall region bordered by the pulmonary vein ostia is isolated from the other atrial tissue. In this process, the mechanical sectioning of atrial tissue eliminates the precipitating conduction to the atrial arrhythmia by creating conduction blocks within the aberrant electrical conduction pathways.

Injection of alcohol into heart tissue has also been employed to ablate cardiac tissue. Alcohol may be delivered to blood vessels supplying the tissue to be ablated, as described in "Transcoronary Chemical Ablation of Arrhythmias", by Nellens et al, Pace Vol. 15, pages 1368–1373, September 1992. Alternatively, alcohol can be delivered directly to the tissue to be ablated by means of a needle inserted through a catheter, as described in "Chemical Ablation by Subendocardial Injection of Ethanol via Catheter—Preliminary Results in the Pig Heart", by Weismuller et al, European Heart Journal, Volume 12, pages 1234–1239, 1991.

Although successful at treating AF, the surgical maze procedure is quite complex and is currently performed by only a few skilled cardiac surgeons in conjunction with other open-heart procedures. Tools that could reliably duplicate the Maze incisions by other means (e.g. radio frequency, laser, microwave, ultrasound energy) will reduce the time and invasiveness required for the maze procedure and make it more accessible to more surgeons. Problems faced by these methods, however, include (a) the creation of continuous, linear lesions in the atria for the prevention of atrial fibrillation, (b) minimization of clotting and thromboembolism, (c) the effect of heat loss due to circulating blood, (d) minimization of lesion width and minimization of atrial debulking, (e) conforming to an irregular myocardial thickness, (f) adaptability to a variety of lesion geometries and (g) usefulness from either the endocardial surface of an open heart, or the epicardial surface of a beating heart.

SUMMARY OF THE INVENTION

The present invention includes devices and methods for ablation of cardiac tissue in which a hand-held, needle-less injector is used to deliver precise amounts of liquid under pressure into cardiac tissue for purposes of ablation of the tissue along a desired lesion line. The liquids can be cytotoxic, protective, and/or conductive and can optionally be used in conjunction with RF current ablation and/or photochemically activated. The injection under pressure can deeply and narrowly ablate cardiac tissue, and can transmurally ablate cardiac tissue entirely through the myocardium when delivered from either the epicardial or the endocardial surface. The needle-less injector device can be a modification of those used for mass vaccinations.

In one embodiment of the invention, the fluid that is injected into the tissue is photo-chemically activated. Light energy can be applied slightly before, during, or after injection of the fluid into the tissue. The distal head of the injection device can incorporate fiber optic electrodes capable of transmitting the appropriate wavelength of energy to the tissue to activate the cytotoxic property of the fluid. Photo-chemically activated fluids are well known, having been used in chemotherapy.

One needle-less, tissue ablative, injector device includes a cylindrical housing having a lumen within for containing a fluid, an electrically conductive distal surface operably coupled to the housing for contacting tissue, and at least one discharge orifice near the electrically conductive surface and in fluid communication with the fluid lumen. The device can also include a pressure applicator in communication with the fluid lumen for imparting sufficient pressure to the fluid lumen to inject the fluid into the myocardium from the epicardial or endocardial surface. A pressure applicator switch operably coupled to the pressure applicator can impart pressure to eject fluid through the discharge orifice when the pressure applicator switch is activated. An electrical connector in electrical continuity with the tissue contacting surface can provide ablative electrical energy to the tissue contacting surface.

Some needle-less tissue ablative injector devices also include a radio-frequency current source electrically coupled to the device electrical connector. Other needle-less injector devices include a fluid supply connector coupled to the fluid lumen. The pressure applicator can include a reciprocating piston slidably disposed within at least part of the fluid lumen. In some devices, a spring urges the piston distally. In other devices, a gas pressure source acts on the piston to move the piston distally. The distal motion of the piston within the fluid lumen can impart high pressure to the fluid in the lumen, forcing the fluid out the discharge orifice and into the tissue.

Needle-less injector devices can also include a distal tip coupled to the device distal region and can have at least one discharge orifice disposed in the tip. The tip can include a fluid lumen coupling the device fluid lumen and the tip discharge orifices, with the tissue contacting surface located on the tip, such that fluid can be injected through at least two discharge orifices simultaneously. In some devices the tip is removable.

Other needle-less injector devices also include an electrical switch electrically coupled to the electrical connector for controllably providing radio frequency energy to the tissue, with the electrical switch being coupled to the pressure applicator switch. Devices can have a two-position trigger configured to first change the state of the pressure applicator switch, and subsequently change the state of the electrical switch. The two-position trigger can cause conductive fluid to be injected into the tissue, followed by application of ablative electrical energy deeply into the tissue, conducted in part by the injected conductive solution.

In one aspect of the invention, a needle-less injector is used to repeatedly penetrate cardiac tissue with fluid under pressure and to deliver a cytotoxic agent into the cardiac tissue. The cytotoxic agent is used to "draw" a lesion on the myocardium by the repeated injection of cytotoxic fluid while moving the tip of the device along the desired lesion pattern. Because of the repeated and rapid injection, the surgeon can complete the lesion pattern rapidly. In some devices, a manually operated switch on the housing of the device activates the pressure applicator as desired by the operator and repeatedly injects fluid under pressure from the device. The fluid pressure can be adjusted to control the depth at which the cytotoxic fluid is delivered to the tissue. The imparted fluid pressure can enable the cytotoxic fluid to be injected into the tissue so that it extends transmurally, through the entire thickness of the tissue. The fluid can be bulk loaded into a fluid reservoir in the device for multiple injections or can be loaded into a "single shot" lumen and repeatedly replenished from an external fluid source. The fluid delivery can be performed endocardially, and/or epicardially on a stopped heart, and/or epicardially on a beating heart.

In yet another aspect of the invention, a device as described above is utilized in combination with radio frequency ablation. The device tissue contacting surface can be connected to one pole of a radio frequency generator while the other pole of the generator is connected to a large indifferent electrode.

In still another aspect of the present invention, the injection head includes two electrodes to create a bipolar ablation device. The electrodes can reside on the surface or penetrate the tissue, using needles for example. The distal ablation head is small in some embodiments, having discrete point or short linear electrodes and only one or a small number of injection orifices. In other embodiments, the ablation head includes longer linear electrodes and a larger number of injection orifices.

Rather than a cytotoxic agent, the high-pressure device can deliver a conductive liquid such as a saline solution that creates an ablative virtual electrode when delivered into the tissue through high pressure. The device is advanced along a desired lesion line on the tissue as the fluid is injected into the tissue. Delivery of the conductive liquid and the ablative radio frequency energy can be synchronized to form the virtual electrode and ablate the tissue along the desired lesion line.

In another aspect of the invention, a device as described above is utilized in combination with a conventional radio frequency ablation device such as the Cardioblate® pen sold by Medtronic, Inc. Rather than a cytotoxic agent, pressure injection delivers a conductive liquid such as a hypertonic saline solution to the tissue. The device is advanced along a desired lesion line on the tissue as the fluid is injected into the tissue. Delivery of the conductive liquid is made into the tissue along the desired lesion line. The conductive tip of the Cardioblate pen is subsequently drawn along the desired lesion line while applying radio frequency energy to the tissue. The hypertonic saline solution that creates a low impedance electrical pathway to ground such that the resultant lesion is deeper and narrower than would normally result from the use of the conventional radio frequency ablation device.

In yet another aspect of the invention, a device as described above is utilized in order to deliver a protective fluid in order to protect certain areas of cardiac tissue, such as tissue near vessels and valves. For example, a hypotonic fluid can be used as a protective fluid in order to increase the electrical impedance of the tissue to be protected relative to the surrounding tissues, essentially insulating the protected tissue from the electrical current of the radio frequency ablation device. This aspect of the invention can be combined with one or more of the other aspects of the invention in which a conductive liquid is delivered to a first portion of cardiac tissue along a desired lesion line and a protective fluid is delivered to a second portion of cardiac tissue spaced apart from the desired lesion line. This can be readily accomplished by a device having a plurality of spaced-apart discharge orifices with centrally located orifices delivering the conductive liquid and other orifices on one or both sides of the centrally located orifices delivering the protective fluid. As the radio frequency ablation device, such as the Cardioblate pen, is advanced along the desired lesion line, a narrower and deeper lesion will result with this technique.

In still another aspect of the invention, a device as described above is utilized in order to deliver an ink or dye to the cardiac tissue in order to identify the position of the lesion line on the cardiac tissue and to identify portions of tissue along the lesion line where the lesion has been completed. For example, the ink or dye can be added to the cytotoxic fluid in order to identify portions of tissue that have received the cytotoxic fluid, and to insure that those portions create a complete lesion along the desired lesion line. Alternatively, the ink or dye can be added to the conductive liquid in order to identify the portions of tissue that have been ablated by the radio frequency energy of a virtual electrode. The completeness of the lesion line is again indicated by the presence of the ink or dye. Alternatively, the ink or dye can be added to the conductive liquid in order to identify the position of the desired lesion line so that the Cardioblate pen or other radio frequency ablation device can be guided along the line that has been established by the delivery of the conductive fluid. In yet another aspect, the ink or dye can be thermochromic such that it changes color when heated to a temperature, which indicates that a lesion has been formed by the application of radio frequency energy. Typically, temperatures above about 50 to 55 degrees C. are required to cause cell death in an ablative lesion made by radio frequency ablation and the thermochromic material would preferably change color in that temperature range.

Other means to drive fluid into tissue can also be used with the present invention. One method includes the use of ultrasound, for example high intensity focused ultra sound (HIFU), to drive a fluid, for example saline, into the tissue. With the addition of a secondary energy source to the device, photophoresis or iontophoresis can be used to help drive fluid into the tissue. If desired, photophoresis and/or iontophoresis may be used alone to drive fluid into the tissue, since photophoresis and/or iontophoresis do not themselves require high-pressure injection.

DETAILED DESCRIPTION OF THE INVENTION

The following detailed description should be read with reference to the drawings, in which like elements in different drawings are numbered identically. The drawings, which are not necessarily to scale, depict selected embodiments and are not intended to limit the scope of the invention. Several forms of the invention have been shown and described, and other forms will now be apparent to those skilled in art. It will be understood that embodiments shown in drawings and described below are merely for illustrative purposes, and are not intended to limit the scope of the invention as defined in the claims, which follow.

Figures 1, 2, 3:
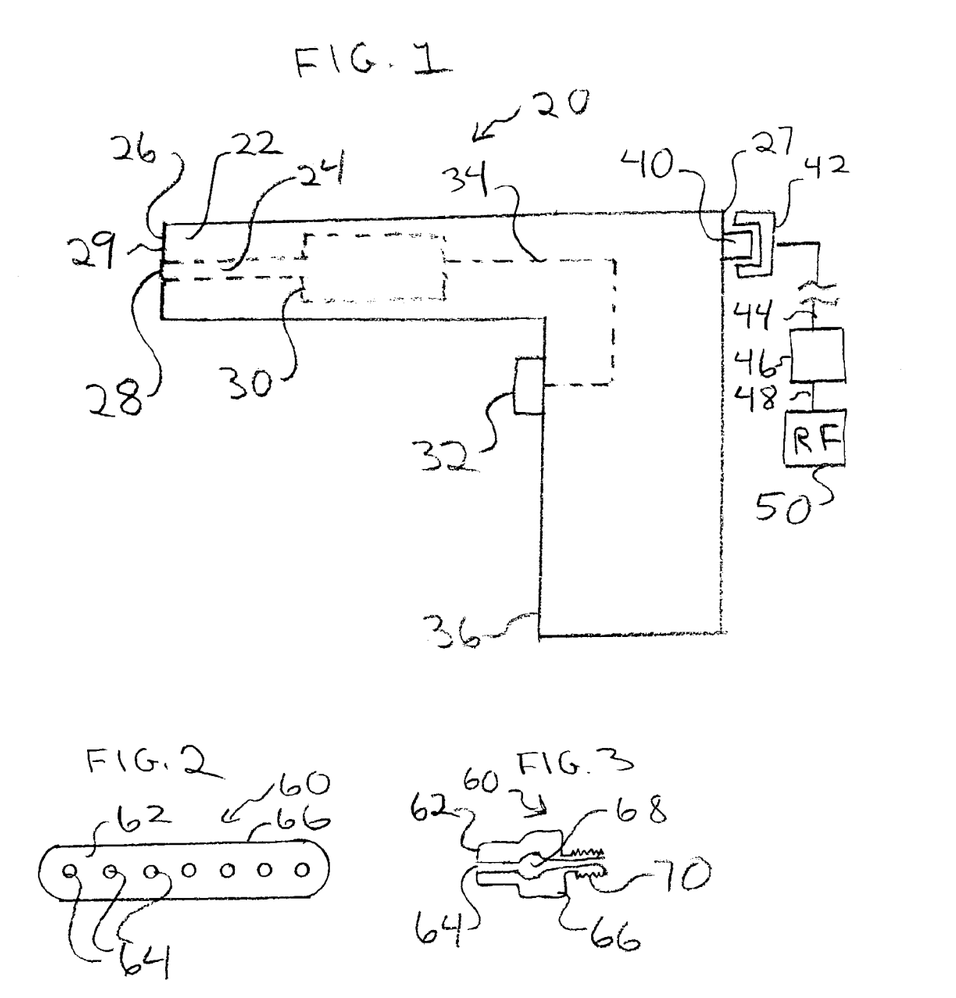
FIG. 1 is a side, schematic view of a needle-less injector device according to the present invention.
FIG. 2 is an end view of a linear array nozzle having multiple discharge orifices according to the present invention.
FIG. 3 is a longitudinal, cross-sectional view of the linear array nozzle of FIG. 2.

FIG. 1 is a schematic view of a needle-less fluid injector device 20 having generally a distal end 26, a proximal end 27, and a handle 36. Needle-less fluid injector 20 includes a barrel or housing 22 having a fluid lumen 24 within. Fluid lumen 24 can terminate distally in a discharge orifice or port 28 and be in fluid communication with a pressure applicator 30. Pressure applicator 30 can include any suitable device for imparting high pressure to the fluid in fluid lumen 24. A pressure applicator trigger 32 may be seen coupled to pressure applicator 30 via a pressure control linkage 34.

When depressed, pressure applicator trigger 32 can initiate the rapid application of pressure to fluid lumen 24 by pressure applicator 30.

Needle-less fluid injector 20 can also include an optional electrical connector 40. Electrical connector 40 can be any suitable electrical connector, including banana plug connectors, screw terminals, spade lugs, jacks, or jack receptacles, as well as other electrical connectors well-known to those skilled in the art. Electrical connector 40 is preferably electrically coupled to tissue contacting surface 29.

FIG. 1 illustrates a radio frequency source electrical connector 42 that is electrically coupled to electrical connector 40. Electrical connector 42 can be coupled via an electrical line 44 to an electrical trigger or switch 46. Electrical trigger or switch 46 is coupled to a radio frequency energy source 50 via another electrical line 48. In some embodiments, electrical switch 46 is external to needle-less fluid injector device 20, for example, a foot switch. In other embodiments, electrical switch 46 is carried on or contained in needle-less fluid injector device 20. In some embodiments, depressing pressure applicator trigger 32 also triggers electrical switch 46. In one device, pressure applicator trigger 32 is a two-position trigger, having a first position for triggering the application of pressure to inject fluid into tissue, followed by a second position for administering ablative radio frequency energy to the tissue now having the injected fluid within.

Fluid can be injected into tissue through discharge orifice 28 while the tissue is contacted by tissue contacting surface 29. Tissue contacting surface 29 can be electrically conductive and in electrical continuity with electrical connector 40. Tissue contacting surface 29 can be part of a distal nozzle region disposed about discharge orifice 28 in some embodiments, and be electrically coupled to electrical connector 40. In another set of embodiments, discharge orifice 28 is coupled to a tip. In this embodiment, the tip itself bears the tissue contacting surface and contains a fluid discharge orifice for injecting fluid under pressure into the tissue.

FIG. 2 illustrates a linear array nozzle 60 for injecting fluid under pressure into tissue from several discharge orifices or ports simultaneously. Linear array nozzle 60 includes generally a body 66, a tissue contacting surface 62, and several discharge orifices 64. FIG. 3 illustrates linear array nozzle 60 from the side, shown in longitudinal cross-section. Linear array nozzle 60 may be seen to also include a manifold 68 for distributing fluid amongst the discharge orifices as well as a threaded connector 70 for connecting to a discharge orifice on a needle-less fluid injector, for example, needle-less fluid injector 20 of FIG. 1. In use, linear array nozzle 60 can be applied to the tissue such that the several discharge orifices 64 are aligned along the desired lesion line. The fluid can then be injected at numerous sites along the desired lesion line at once, speeding the lesion-creating process.

Figure 4:
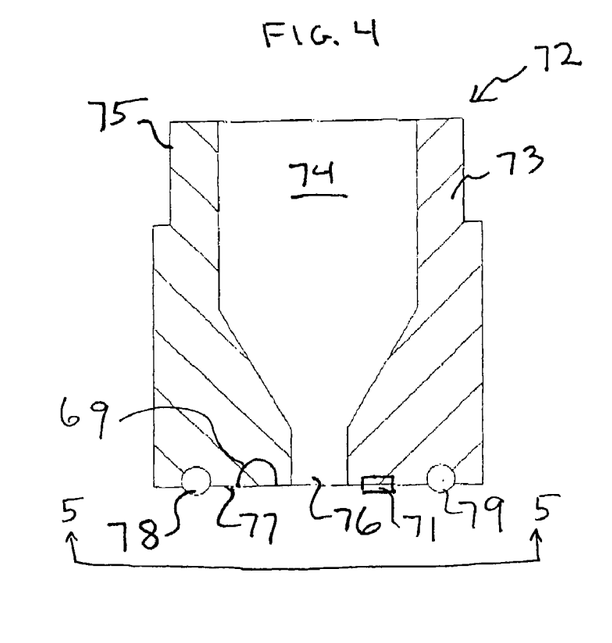
FIG. 4 is a transverse, cross-sectional view of a bi-polar injection nozzle having short linear electrodes.
Figure 5:
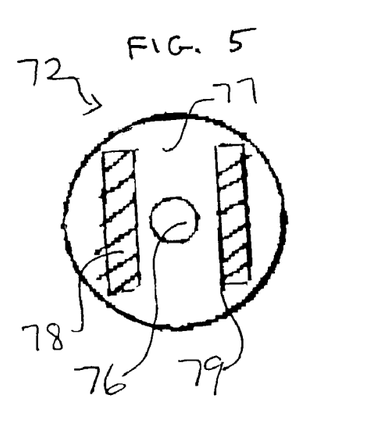
FIG. 5 is a bottom view of the bi-polar injection nozzle of FIG. 4.

FIGS. 4 and 5 illustrate a bi-polar injection nozzle 72 that can be used without an external indifferent electrode. Bi-polar injection nozzle 72 includes a non-conductive body 73 having a fluid lumen 74 within and terminating in a fluid injection orifice 76. Orifice 76 is disposed within a tissue contacting surface 77. Nozzle 72 also includes a tissue proximity sensor 71 mounted in tissue contacting surface 77. Tissue proximity sensor 71 can be used to sense the presence of tissue to ensure that nozzle 72 is disposed near the tissue before ejection of fluid and/or application of RF energy are allowed. Tissue sensor 71 can be a sensor that measures impedance, capacitance, pressure, or other properties, and can be a mechanical sensor in some embodiments. As used herein, the term "tissue sensor or tissue proximity sensor" refers to a sensor that senses the presence of tissue, but may also sense other surfaces and still be considered a tissue sensor. In one example, a mechanical or solid state pressure switch would trigger on any applied pressure, and would still be considered a tissue sensor. The tissue sensor can be used to control or bias a relay or gate to require that the nozzle be pressed against something or near something in order for fluid to be injected and/or RF energy applied. A suction pod or vacuum orifice 69 is also shown on tissue contacting surface 77. In one embodiment, one or more vacuum pods are present on, and can even encircle the nozzle. The vacuum pods can be coupled to a vacuum lumen (not shown in FIG. 4). The vacuum pods can aide in holding the nozzle firmly against the tissue. Holding the nozzle steady and making sure the nozzle is disposed against the tissue can reduce any irritation that might be caused by ejecting fluid while moving the nozzle.

Tissue contacting surface 77 of nozzle 72 also includes a first polarity electrode 78 and a second polarity electrode 79. Electrodes 78 and 79 can be either relatively short linear electrodes as illustrated in FIG. 5, point electrodes, or elongate electrodes intended for use with multiple orifices.

Figure 6:
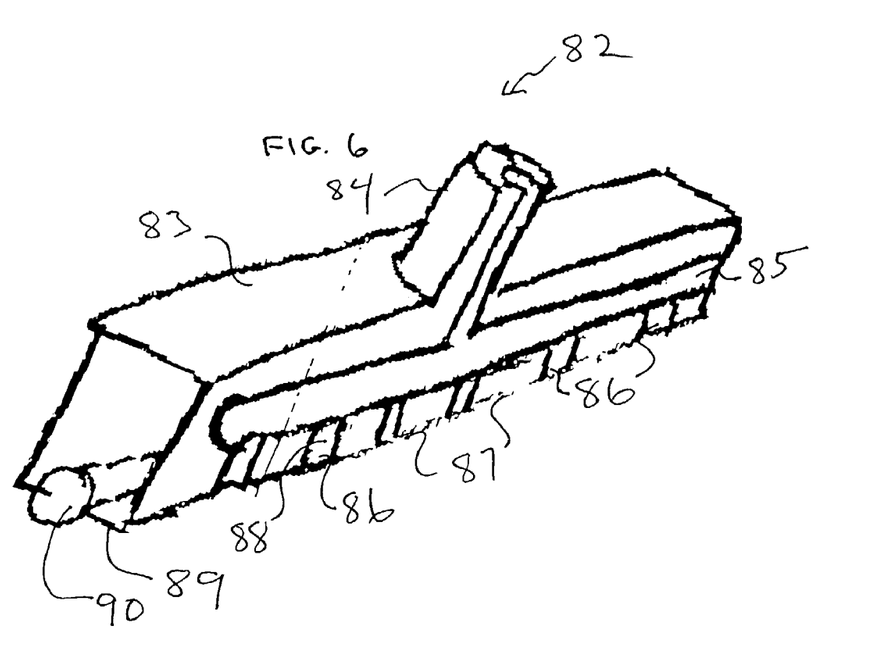
FIG. 6 is a transverse, cut-away view of a bi-polar injection nozzle having numerous injection orifices and elongate electrodes.

FIG. 6 illustrates a bi-polar, linear array nozzle 82, having a non-conductive body 83 housing a fluid lumen 85. Lumen 85 feeds several nozzle supply lumens 88 that in turn supply fluid discharge orifices 86 positioned along a tissue contacting surface 87. Nozzle 82 includes a stem or shoulder region 84 that can be threaded or otherwise configured for attachment to a fluid injection device. The tissue contacting surface 87 of nozzle 82 includes two, opposite polarity electrodes, arranged on opposite sides of the linear array of orifices 86, one of the electrodes, electrode 90, is illustrated in FIG. 6. Electrode 90 is disposed within a nozzle region 89. Electrode 90 is an elongate electrode, extending along the numerous discharge orifices 86. In one embodiment of the invention, nozzle 82 is between about 5 and 7 centimeters long, and has between about 4 and 8 discharge orifices. Nozzle 82 can be used without an external indifferent electrode, and can be used to inject multiple tissue locations simultaneously. In another embodiment, not requiring separate illustration, a second manifold is provided to supply some of discharge orifices 86. In one example, a first manifold supplies orifices near stem 84 and the second manifold supplies orifices further from stem 84. In one example of use, an ablative fluid is injected from a centrally located orifice and a protective fluid is injected from orifices located on one or both sides of the central orifice.

Figure 7:
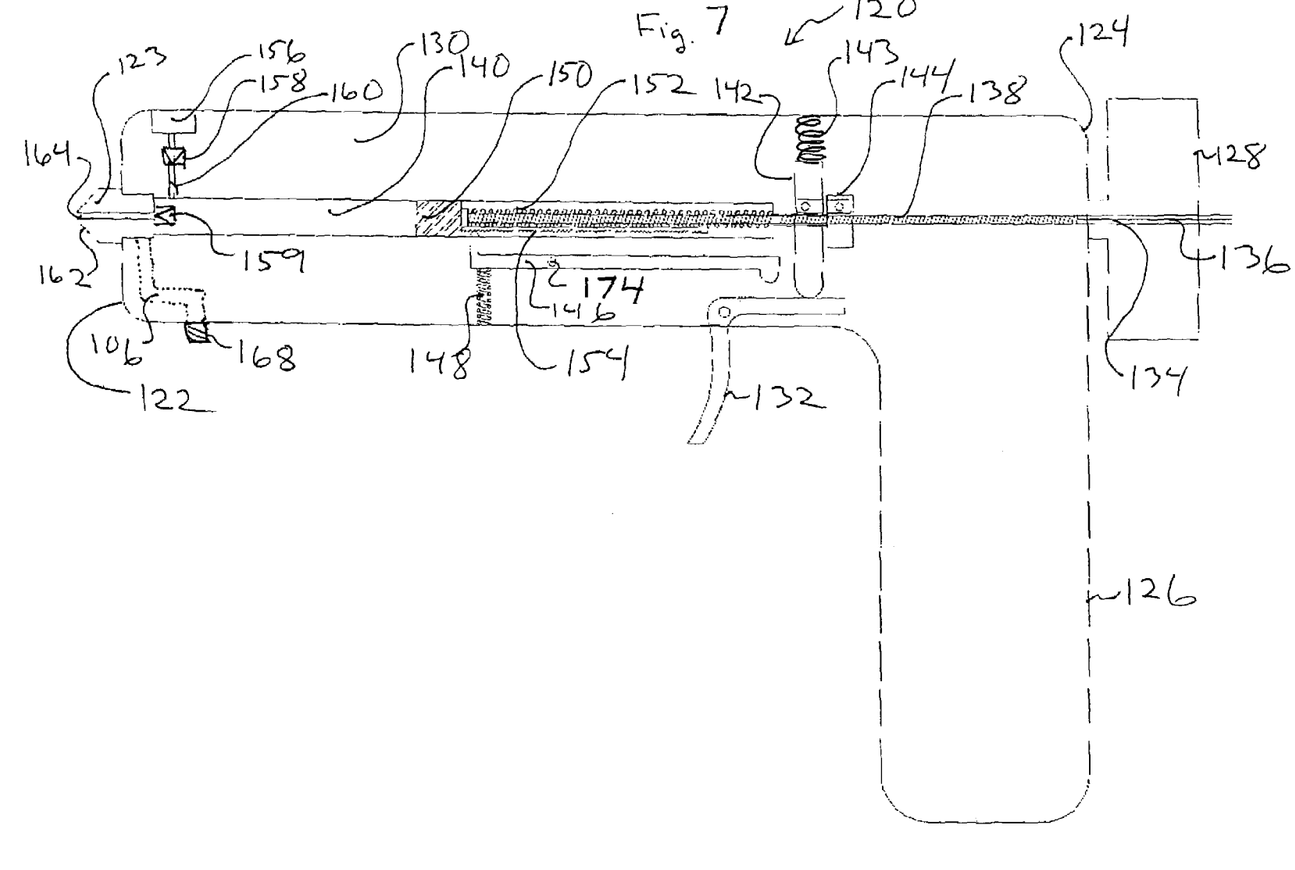
FIG. 7 is a diagrammatic, longitudinal cross-sectional view of a needle-less injector device having a spring loaded pressure applicator.

FIG. 7 illustrates another needle-less injector 120, having a spring-loaded, mechanical pressure applicator. Needle-less injector 120 includes a distal end region 122, a proximal end region 124, a handle 126, a housing or barrel 130, and a distal tip 123. Tip 123 includes a fluid discharge orifice or port 164 and a tissue-contacting surface 162. Optionally, tip 123 can be electrically conductive. Tip 123 can be connected to conductor 106, which is electrically coupled to an electrical connector 168. External radio frequency (RF) ablation energy sources can be connected to electrical connector 168.

Needle-less injector 120 includes a fluid lumen 140 for containing the fluid to be injected. Fluid lumen 140 can be coupled to a supply lumen 160 which can in turn be coupled to a check valve 158. Check valve 158 can be supplied by a fluid loading port 156. In some embodiments, a distal check valve 159 is disposed between fluid lumen 140 and fluid discharge orifice 164. A piston 150 may be seen in fluid communication with fluid lumen 140.

A shaft 134 is shown in FIG. 7, having a proximal hexagonal cross-sectional portion 136 and a more distal threaded portion 138. A rotatable knob 128 can be disposed about shaft hexagonal portion 136. Shaft 134 can extend through a split-nut 144 coupled to a split-nut actuator 142. Split-nut actuator 142 can be maintained in a closed, thread engaging position by a biasing spring 143. Shaft 134 extends further distally through a compression spring 152, with shaft 134 being coupled to piston 150 near the shaft distal region. Mechanical elements referenced but not discussed with respect to FIG. 7 are shown and discussed with respect to FIG. 8.

Figure 8:
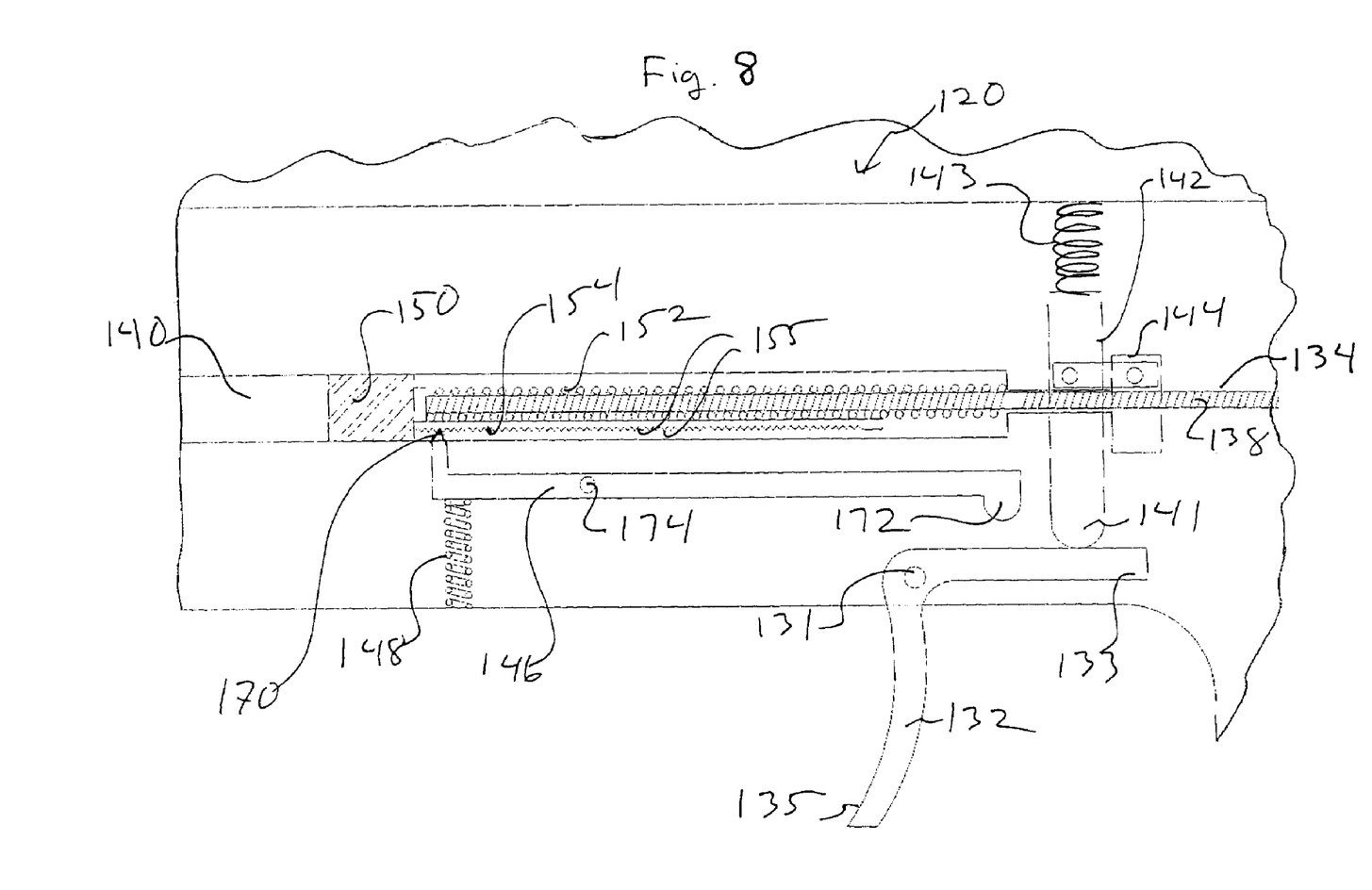
FIG. 8 is a fragmentary, longitudinal cross-sectional detail view of the needle-less injector device of FIG. 7.

FIG. 8 illustrates the mechanical actuating elements of needle-less injector 120 in more detail. A retention rack 154 may be seen coupled at its distal end to piston 150. Retention rack 154 may be seen to have a plurality of teeth 155. A piston retainer 146 may be seen pivotally mounted about pivot 174 and having a pawl 170 for engaging retention rack 154 as well as a more proximal cam or actuator end 172. A keeper spring 148 may be seen biasing pawl 170 to engage retention rack teeth 155. A trigger 132 may also be seen, mounted about a pivot 131 and having a manually operable portion 135 and an actuator portion 133 disposed near an actuator end 141 of split-nut actuator 142.

The operation of needle-less injector device 120 can be visualized with respect to FIGS. 7 and 8. In use, needle-less injector device 120 can be "cocked" by proximally retracting shaft 134, thereby compressing spring 152 and proximally retracting piston 150 to create fluid containing space within fluid lumen 140. In devices having check valve 159, check valve 159 can prevent air from being pulled into fluid lumen 140. A fluid supply tube can be coupled to fluid loading port 156, and fluid forced through check valve 158 and supply lumen 160 into fluid lumen 140. Check valve 158 can later prevent fluid from being ejected out through fluid loading port 156, rather than into the tissue as desired.

Shaft 134 can be proximally retracted in various ways in various embodiments. In the embodiment illustrated in FIG. 7, knob 128 can be rotated. Knob 128, having a hexagonal shaped internal opening to mate to the outside of shaft hexagonal portion 136, can apply torque to shaft 134 and thereby rotate shaft 134. The rotating shaft 134 threaded portion 138 passes through split-nut 144, with the nut being in the closed, thread engaging position. Knob 128 can thus be rotated to proximally retract shaft 134 by engaging the internal threads of split-nut 144. In some embodiments, the functionality of knob 128 is either assisted or replaced by a motor-driven element for rotatably engaging shaft 134. In some embodiments, teeth 155 on retention rack 154 may be angled to allow the proximal retraction of shaft 134 while engaged by pawl 170. In other embodiments, trigger 132 may be pulled while retracting shaft 134. With shaft 134 in a proximally retracted position, and fluid lumen 140 containing fluid, the device is prepared to inject fluid.

Trigger manually operable portion 135 can be pulled, thereby urging trigger actuator end 133 against split-nut actuator end 141, to urge split-nut actuator 142 against biasing spring 143. Split-nut actuator 142 thus opens split nut 144 to disengage shaft threaded portion 138, leaving retention rack teeth 155 engaged by pawl 170. As trigger 132 is further depressed, trigger actuator end 133 can engage piston retainer cam region 172 to pivot piston retainer 146 about pivot 174 and thereby disengage pawl 170 from teeth 155. Spring 152 can now drive piston 150 against the fluid contained within fluid lumen 140 to force the fluid through discharge orifice 164. In other embodiments, knob 128 can be replaced by a lever-cam device, for rapidly retracting shaft 134 in a single motion.

In embodiments utilizing only a cytotoxic fluid, and not utilizing radio frequency (RF) ablation, a device performing the functions of needle-less injector device 120 may be sufficient to form a lesion along the desired lesion line. In embodiments utilizing RF ablation, an external RF ablation source can be connected to electrical connector 168 to supply tissue-contacting surface 162 with radio frequency ablation energy. In some devices, an external trigger or switch is used to control the application of radio frequency ablation energy to the tissue. In other embodiments, an electrical switch can be operably coupled to trigger 132, such that the action of trigger 132 triggers both the fluid injection and the application of radio frequency ablating energy to the tissue. The application of radio frequency energy to the tissue can be slightly delayed to allow the injection of fluid into the tissue prior to the application of the radio frequency energy.

Figure 9:
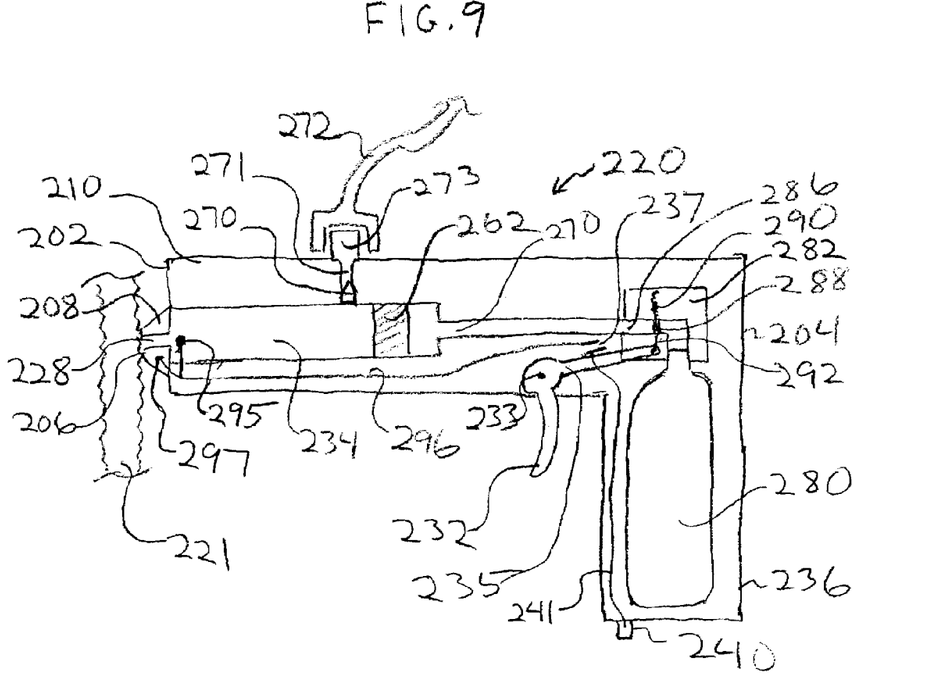
FIG. 9 is a highly diagrammatic, longitudinal cross-sectional view of a needle-less injector device having a high pressure, gas-pressurized applicator.

FIG. 9 illustrates a gas pressure operated needle-less fluid injector 220. Needle-less injector device 220 may be seen to extend from a distal region 202 to a proximal region 204 and have a handle 236. Needle-less injection device 220 includes a distal tip 208 having a fluid discharge orifice 228 and a distal tissue-contacting surface 206. Distal tip 208 may be seen contacting tissue 221. Needle-less injection device 220 also includes a barrel or housing 210 having a fluid chamber or fluid lumen 234 within. Fluid lumen 234 may be seen coupled to a check valve 270, which is in turn coupled through a supply lumen 271 to a fluid coupling 273. Fluid coupling 273 may be seen connected to an external fluid source 272.

A high-pressure gas source or cylinder 280 may be seen within handle 236. High pressure gas source 280 is coupled to a valve body 282 having a valve channel 286 therethrough reversibly blocked by a valve stem or plug 288.

Valve plug 288 is coupled to a tension biasing spring 290 to maintain the valve plug in the closed position. A trigger 232 may be seen including a lever arm 235 pivotally mounted about pivot point 233. Lever arm 235 is coupled to valve plug 288 through a rod 292. Valve body 282 is a coupled to a piston 262 through a gas channel 270. Piston 262 can be slidably and sealingly disposed within fluid lumen 234.

Needle-less injection device 220 can also include an electrical line 296 coupled to distal tip 208 at 297 and to tissue contacting surface 206. Electrical line 296 is also connected to a lumen contacting electrode 295. Devices can have the electrical source in contact with the tissue contacting surface, a conductive fluid within the fluid lumen, or both. Electrical line 296 is coupled through an electrical switch 237 to a second electrical line 241 which is in turn electrically coupled to an electrical connector 240. Electrical connector 240, as previously discussed with respect to connector 40 of FIG. 1, can be any suitable connector for coupling tip 208 to an external RF energy ablation source. Electrical switch 237 can be disposed near trigger lever arm 235 so as to be closable by trigger action from trigger 232. In some embodiments, trigger 232 is configured to release high-pressure gas against piston 262 in a first degree of movement, and to close electrical switch 237 with a second, greater degree of movement. This two-position trigger allows the initial injection of fluid into myocardial tissue followed by the subsequent delivery of radio frequency current into the already-injected tissue.

In use, fluid can be supplied by fluid source 272, through fluid coupling 273, and through check valve 270 into fluid lumen 234, thereby forcing piston 262 proximally away from distal tip 208, and filling fluid lumen 234 with fluid. Distal tip 208 can be disposed against tissue 221 and trigger 232 depressed to a first position, moving valve plug 288 out of valve channel 286 to allow high pressure gas to flow from high pressure gas source 280 through gas channel 270 to drive piston 262 against fluid contained in fluid lumen 234. The driving piston 262 thus forces fluid out of fluid lumen 234, through fluid discharge orifice 228, and into tissue 221. Trigger 232 can then be depressed to a second, more depressed position to close electrical switch 237, providing radio frequency ablative energy to tissue contacting surface 206. Ablative electrical energy can thus be provided to the tissue region recently injected with fluid. As previously discussed, the fluid can be a conductive fluid, thus forming a virtual electrode in the tissue.

Many presently available vaccination guns can be used to practice one aspect of the present invention. Specifically, applicants believe that presently available vaccination guns can be used to inject cytotoxic fluids into the myocardial tissue as well as other tissues to be injected with cytotoxic fluids. Presently available vaccination guns may also be used by modifying the guns to provide ablative, radio frequency energy at or near the distal, tissue contacting surface or tip. Some vaccination guns can be modified by adding an electrical connector electrically coupled to the conductive, distal tip. An external radio frequency energy source can then be connected to the gun electrical connector to practice the ablative, radio frequency energy aspect of the present invention to form tissue legions in the target tissue.

The depth of penetration of the fluid injected can be adjusted to match the target tissue thickness and the desired degree of penetration. In myocardial applications, it may be desirable to have the fluid penetrate at least about halfway through the tissue thickness without penetrating entirely through the tissue thickness. In some methods, the fluid pressure can be set to effect transmural penetration. The penetration depth can be controlled by adjusting the pressure applied by the pressure applicator. In mechanical embodiments of the present invention, the pressure may be adjusted by varying the degree of compression supplied to a spring within the needle-less injector device. In gas-operated embodiments, the pressure may be varied by regulating the gas pressure supplied at the piston. In one embodiment of the invention, an ultrasonic transducer can be mounted near the device distal end to provide an indication of tissue thickness near the tip, and the fluid penetration depth set as a function of the indication of tissue thickness.

The cytotoxic agents referred to in the present application are agents that have cytotoxic properties and can be delivered as injectable liquids or as liquid suspensions. Preferably, a cytotoxic substance has potent cytotoxic properties that destroy cell function without affecting protein structure and scaffolding. The cytotoxic agent also preferably has limited and controllable diffusion properties through extracellular spaces. Also, the cytotoxic agent preferably has a fleeting effect such that the compound washes out of the systemic circulation quickly. Alkylating agents such as cytotoxin or melphalan or their active metabolites are preferred.

Figure 10:
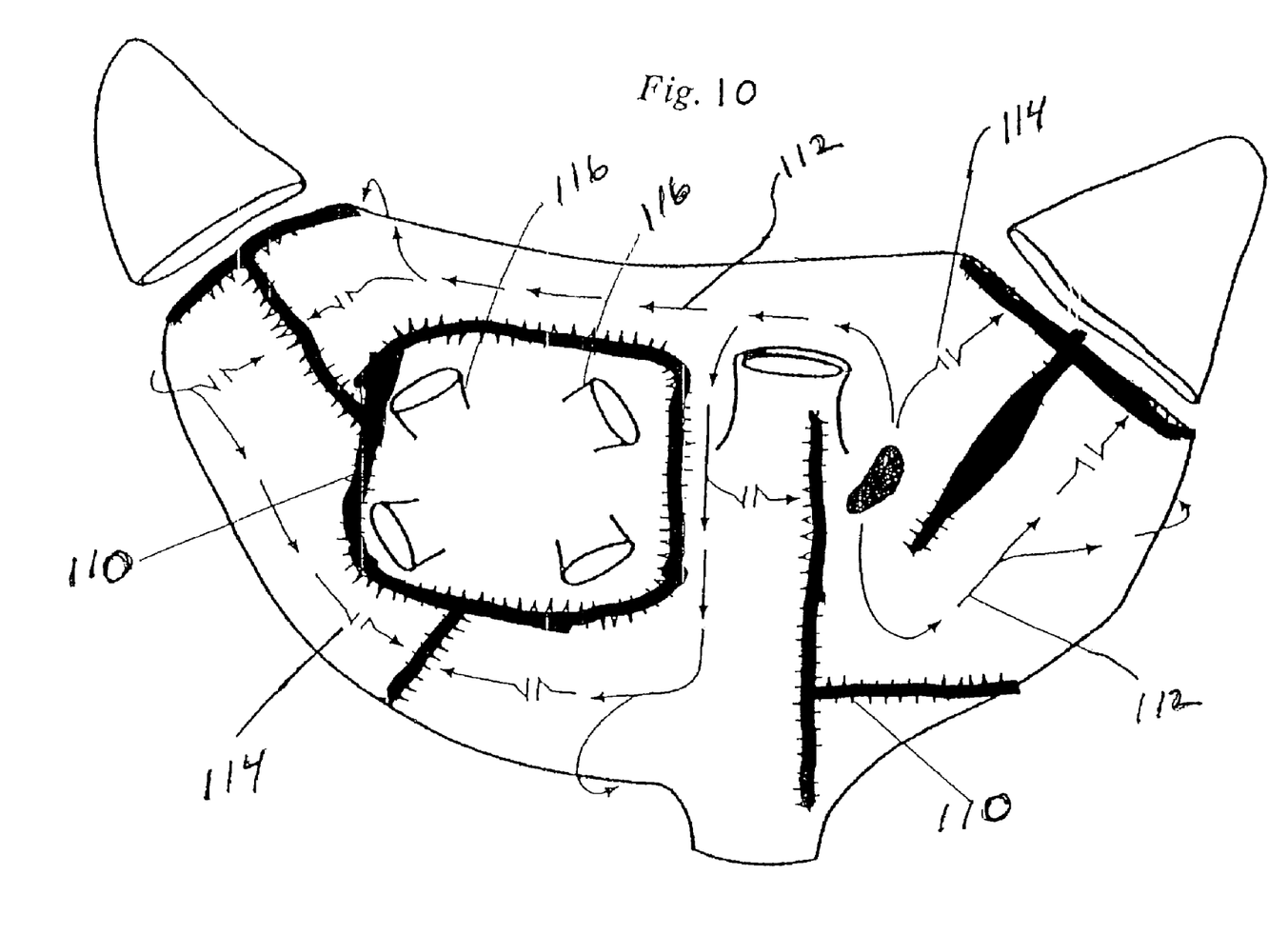
FIG. 10 is a schematic view of the heart showing various maze lesions that can be formed according to the invention.

FIG. 10 illustrates some possible generally linear lesion patterns 110 that are capable of interrupting conductive pathways 112 and 114. The lesion patterns can be made as described above or in combination with a conventional radio frequency ablation device such as the Cardioblate pen sold by Medtronic, Inc. (not shown). Rather than a cytotoxic agent, a device delivers a conductive liquid such as a hypertonic saline solution to the tissue. The device is advanced along a desired lesion line 110 on the tissue as the high-pressure fluid is forced into the tissue. Delivery of the conductive liquid is made into the tissue along the desired lesion line 110. The conductive tip of the Cardioblate pen can then be drawn along the desired lesion line 110 while applying radio frequency energy to the tissue. The hypertonic saline solution creates a low impedance electrical pathway from the conductive tip to the ground electrode such that the resultant lesion is deeper and narrower than would normally result from the use of the conventional radio frequency ablation device.

A protective fluid can also be used when making the linear lesions 110 in order to protect certain areas of cardiac tissue, such as tissue near vessels and valves like the pulmonary veins 116. For example, a hypotonic fluid can be used as a protective fluid in order to increase the electrical impedance of the tissue to be protected relative to the surrounding tissues, essentially insulating the protected tissue from the electrical current of the radio frequency ablation device. Alternatively, the protective fluid can be a thermally protective fluid such as a chilled fluid, which protects tissue adjacent to the intended lesion from being overheated. This aspect of the invention can be combined with one or more of the other aspects of the invention in which a conductive liquid is delivered to a first portion of cardiac tissue along a desired lesion line and a protective fluid is delivered to a second portion of cardiac tissue spaced apart from the desired lesion line. This can be readily accomplished by a device having a plurality of spaced-apart discharge orifices with centrally located orifices delivering the conductive liquid and other orifices on one or both sides of the centrally located orifices. As the radio frequency ablation device, such as the Cardioblate pen, is advanced along the desired lesion line a narrower and deeper lesion would result with this technique.

Also, the device as described above can be utilized in order to deliver an ink or dye to the cardiac tissue in order to identify the position of the lesion line 110 on the cardiac tissue and to identify portions of tissue along the lesion line 110 where the lesion has been completed. For example, the ink or dye can be added to the cytotoxic fluid in order to identify portions of tissue which have received the cytotoxic fluid and that those portions create a complete lesion along the desired lesion line. Alternatively, the ink or dye can be added to the conductive liquid in order to identify the portions of tissue, which has been ablated by the radio frequency energy of a virtual electrode. Again the completeness of the lesion line is indicated by the presence of the ink or dye. Alternatively, the ink or dye can be added to the conductive liquid in order to identify the position of the desired lesion line so that the Cardioblate pen or other radio frequency ablation device can be guided along the line that has been established by the delivery of the conductive fluid. Dyes such as those used for tattoos are believed suitable, as are some tissue dyes. Toluene blue and methylene blue are examples of dyes believed suitable for use in the present invention.

In yet another aspect, the ink or dye can be thermochromic such that it changes color when heated to a temperature, which indicates that a lesion has been formed by the application of radio frequency energy. Typically, temperatures above about 50 to 55 degrees C. are required to cause cell death in an ablative lesion made by radio frequency ablation and the photochromic material would preferably change color in that temperature range.

In still another aspect, the injected fluid can include a viscosity enhancing agent or fluid added to reduce or retard fluid diffusion after delivery. Reducing the diffusion of a cytotoxic and/or conductive fluid can reduce the width of the resulting lesion. Reducing the diffusion of a protective fluid can maintain the protective fluid in a desired position adjacent the cytotoxic and/or conductive fluid, to serve its protective function. Viscous fluids such as dextrose or glycerol may be added to increase the viscosity of a delivered fluid. The viscous fluids or agents can provide a fluid viscosity of at least about twice that of water.

In still another aspect, the delivery of ionized fluids may be enhanced via a small current applied across two electrodes, i.e., iontophoresis. For example, a small current applied between the conductive distal tip 208 of needle-less injection device 220 and the ground electrode can enhance the movement within tissue of ionized fluid delivered from the fluid discharge orifice 228. As an alternative to a mono-polar configuration, a bi-polar configuration could be used. For example, a small current may be applied between electrode 78 of nozzle 72 and electrode 79 of nozzle 72. As described above, electrodes 78 and 79 can be either relatively short linear electrodes as illustrated in FIG. 5, point electrodes, or elongate electrodes intended for use with multiple fluid discharge orifices. Positive ions may be introduced into tissue from the positive pole or electrode, or negative ions from the negative pole or electrode. The use of iontophoresis can markedly facilitate the transport of certain ionized molecules.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

The invention claimed is:

1. A needle-less tissue ablative injector device for injecting a fluid into cardiac tissue, the device comprising:
    a housing having a lumen within for containing the fluid;
    a distal surface operably coupled to the housing for contacting cardiac tissue;
    at least one discharge orifice disposed near the distal surface and in fluid communication with the fluid lumen;
    a pressure applicator in communication with the fluid lumen for imparting sufficient pressure to the fluid lumen to inject the fluid into myocardium from an epicardial surface;
    a pressure applicator switch operably coupled to the pressure applicator for controllably imparting pressure from the pressure applicator to the fluid lumen when the pressure applicator switch is activated;
    a first electrode disposed to contact at least one of the tissue and the fluid lumen;
    an electrical connector in electrical continuity with the first electrode for providing ablative electrical energy to the cardiac tissue;
    an electrical switch operably coupled to the electrical connector for controllably providing the ablative electrical energy to the cardiac tissue when the electrical switch is activated; and
    a switch member operably configured to first activate the pressure applicator switch to cause fluid to be injected into the myocardium and subsequently to activate the electrical switch to cause ablative electrical energy to be provided to the cardiac tissue having the injected fluid within, wherein depressing a portion of the switch member to a first position activates the pressure applicator switch and further depressing the same portion of the switch member to a more depressed second position activates the electrical switch.

2. A needle-less tissue ablative injector device as in claim 1, further comprising a radio-frequency current source electrically coupled to the electrical connector.

3. A needle-less tissue ablative injector device as in claim 1, further comprising a fluid supply connector coupled to the fluid lumen.

4. A needle-less tissue ablative injector device as in claim 1, wherein the pressure applicator includes a reciprocating piston, wherein the reciprocating piston is disposed within the fluid lumen.

5. A needle-less tissue ablative injector device as in claim 4, further comprising a spring urging the piston to travel distally.

6. A needle-less tissue ablative injector device as in claim 4, further comprising a gas pressure source urging the piston to travel distally.

7. A needle-less tissue ablative injector device as in claim 1, further comprising a distal tip coupled to the device distal region, wherein the at least one discharge orifice numbers at least two and the orifices are disposed in the tip, wherein the tip includes a tip fluid lumen in fluid communication with the device fluid lumen and the tip discharge orifices, wherein the distal surface is located on the distal tip, such that fluid can be injected through at least two discharge orifices simultaneously.

8. A needle-less tissue ablative injector device as in claim 7, wherein the distal tip is removable from remaining portions of the injector device.

9. A needle-less tissue ablative injector device as in claim 1, wherein the device further comprises a second electrode electrically isolated from the first electrode to form a bi-polar tissue ablating device.

10. A needle-less tissue ablative injector device as in claim 1, wherein the fluid is capable of being delivered to the myocardium in a predetermined, metered amount.

11. A needle-less tissue ablative injector device as in claim 1, wherein the device is adapted to be used epicardially on a beating heart.

12. A needle-less tissue ablative injector device as in claim 1, wherein the device is capable of injecting fluid into at least half the thickness of the myocardium.

13. A needle-less tissue ablative injector device as in claim 1, wherein the fluid is a conductive fluid.

14. A needle-less tissue ablative injector device as in claim 1, wherein the switch member is a two-position switch member.

15. A needle-less tissue ablative injector device as in claim 14, wherein the two-position switch member is a two-position trigger.

16. An ablation device for ablating cardiac tissue, the device comprising:
    a housing having a lumen within for containing a conductive fluid;
    a distal surface operably coupled to the housing for contacting tissue to be ablated;
    a discharge orifice disposed near the distal surface and in fluid communication with the fluid lumen;

a pressure applicator operably coupled to the fluid lumen for applying sufficient pressure to the conductive fluid to inject the conductive fluid into tissue;

a pressure applicator switch operably coupled to the pressure applicator for controllably applying pressure from the pressure applicator to the conductive fluid when the pressure applicator switch is activated;

a first electrode disposed to contact at least one of the tissue and the fluid lumen;

a radio-frequency current source operably coupled to the first electrode for providing ablative electrical energy to the cardiac tissue; and an electrical switch operably coupled to the electrical connector for controllably providing the ablative electrical energy to the cardiac tissue when the electrical switch is activated, wherein the electrical switch is operably coupled to the pressure applicator switch to cause ablative electrical energy to be provided to the cardiac tissue following the injection of conductive fluid into tissue; and a switch member operably coupled to the pressure applicator switch and the electrical switch, wherein depressing a portion of the switch member to a first position activates the pressure applicator switch and further depressing the same portion of the switch member to a more depressed second position activates the electrical switch.

* * * * *